United States Patent [19]

Larkins, Jr.

[11] 4,374,265

[45] Feb. 15, 1983

[54] PREPARATION OF ETHYLIDENE DIACETATE

[75] Inventor: Thomas H. Larkins, Jr., Kingsport, Tenn.

[73] Assignee: Eastman Kodak Company, Rochester, N.Y.

[21] Appl. No.: 288,830

[22] Filed: Jul. 31, 1981

[51] Int. Cl.$^3$ ...................... C07C 67/00; C07C 69/16
[52] U.S. Cl. ................................... 560/263; 260/549; 560/265; 562/607
[58] Field of Search ............................. 560/263, 112; 260/410.6

[56] References Cited

U.S. PATENT DOCUMENTS 3,579,566  5/1971  Fenton ................................ 560/263
3,957,827  5/1976  Lyons ................................. 560/263
4,221,918  9/1980  Suzuki ................................ 560/263

Primary Examiner—Vivian Garner
Attorney, Agent, or Firm—David E. Cotey; Daniel B. Reece, III

[57] ABSTRACT

Process for the preparation of ethylidene diacetate by hydrogenating acetic anhydride in the presence of a heterogeneous palladium catalyst and a silica-alumina material.

6 Claims, No Drawings

PREPARATION OF ETHYLIDENE DIACETATE

This invention relates to a novel process for the preparation of ethylidene diacetate by hydrogenating acetic anhydride.

An economically advantageous process for the preparation of acetic anhydride by the carbonylation of methyl acetate has been reported in the patent literature. See, for example, Belgian Patent 819,455, British Published patent application No. 2,013,184, Japanese Published patent application Nos. 75-47921 and 75-47922 and U.S. Pat. Nos. 3,927,078 and 4,046,807. Not only is acetic anhydride itself an important chemical, for example as an acetylating agent in the manufacture of cellulose acetate and other esters, but it can be converted to ethylidene diacetate. The ethylidene diacetate can be converted to vinyl acetate which, at the present time, is derived primarily from petroleum.

U.S. Pat. No. 4,221,918 discloses the preparation of ethylidene diacetate by hydrogenating acetic anhydride in the presence of a heterogeneous palladium catalyst and a strong protonic acid that is soluble in the reaction medium, e.g., in acetic anhydride. The ethylidene diacetate so produced normally must be purified by distillation. Due to ethylidene diacetate being very sensitive to traces of acid, a substantial portion of it decomposes to acetic anhydride, acetaldehyde, vinyl acetate, acetic acid and tar during distillation. Neutralization of the acid not only creates waste salts that must be disposed of but fails to overcome the decomposition problem, perhaps because of a salt-acid equilibrium.

The process of this invention comprises hydrogenating acetic anhydride at elevated pressure and temperature in the presence of a catalytic amount of a heterogeneous palladium catalyst and a silica-alumina material. Both the heterogeneous palladium catalyst and the acidic silica-alumina material may be separated from the crude product mixture which can then be distilled to recover the ethylidene diacetate free from other compounds present. The palladium catalyst and silica-alumina may be used separately, i.e., as a physical mixture, or may be used in a combined form, i.e., a supported catalyst consisting of a silica-alumina support on which is deposited palladium metal or palladium oxide.

The process can be carried out either by batch or continuous operation, for example, by continuously feeding acetic anhydride and hydrogen to a stirred pressure vessel and continuously removing crude product by means of a filter leg. Continuous operation advantageously can be carried out using a columnar hydrogenation reactor containing one or more fixed beds of a palladium on a silica-alumina support. Acetic anhydride is fed to the column wherein it is hydrogenated at elevated temperature and pressure. Co-product acetic acid and any acetic anhydride present in the reactor effluent are separated from the ethylidene diacetate and the anhydride may be recycled to the reactor. The acetic acid produced may be esterified with methanol and the resulting methyl acetate used to produce acetic anhydride.

In addition to catalyst, silica alumina and acetic anhydride, the feed to the hydrogenation reactor can contain other materials. For example, if the process of this invention is integrated with a process for manufacturing acetic anhydride by the carbonylation of methyl acetate in the presence of acetic acid solvent, the feed may also contain methyl acetate and acetic acid. The concentration of each can vary substantially depending on such factors as the degree of methyl acetate conversion, the amount of acetic acid employed and the product isolation technique used in the anhydride process. Normally, the concentration of the low boiling methyl acetate in the feed to the hydrogenation reactor can be minimized by removing it from the effluent from the carbonylation reactor in which acetic anhydride is produced.

Examples of the heterogeneous palladium hydrogenation catalysts that can be employed in the process of this invention include palladium oxide and supported palladium catalysts such as palladium on carbon, alumina, refractory materials, silica and, as described above, silica-alumina. In operations in which a palladium catalyst and the silica-alumina are used separately, the supported palladium catalysts generally are the most suitable with palladium on alumina and, especially, palladium on carbon being preferred. By characterizing the catalysts as heterogeneous, it is meant that the catalysts are insoluble in the reaction medium and remain essentially insoluble during the practice of the hydrogenation process, both under batch and continuous operation.

The catalytically-effective amount of the heterogeneous palladium catalyst that will give satisfactory results depends on a great number of variables. For example, the optimum amount of catalyst will depend on reaction conditions such as temperature, pressure and flow rates, the particular catalyst used, the amount of silica-alumina present, the composition of the silica-alumina material, and the mode of operation of the process. For example, in a batch process employing a catalyst slurry a particular or predetermined amount of catalyst may be used whereas in a continuous process employing one or more fixed beds of catalyst, the concentration of catalyst relative to the feed to the hydrogenation reactor cannot precisely be defined. The particular support chosen and the amount and surface area of the palladium on the supported catalysts and the technique by which the palladium is deposited on the support also would be expected to affect catalyst activity and thus the amount of the supported catalyst required to give a desired yield and/or production rate.

The hydrogenation-effective temperature and pressure which can be used in the process also will vary considerably since not only are they interdependent but each, especially temperature, is dependent on the amount of silica-alumina material employed. Suitable temperature and pressure ranges are about 100° to 200° C. and about 250 to 3000 psig total reaction pressure. The preferred ranges are about 130°–160° C. and 500–1200 psig.

The silica-alumina material may be a naturally occurring material such as keiselguhr and montmorallite clay or it may be a synthetic silica-alumina material such as those used as cracking catalysts in the petroleum industry. The silica-alumina may contain from about 5 to 40 weight percent alumina, the remainder being essentially all silica. The silica-alumina may contain minor amounts, e.g., up to about 10 weight percent, of other elements. The silica-alumina material preferably consists of silica ($SiO_2$) containing about 15–30 weight percent of alumina ($Al_2O_3$). The acidifying-effective amount of the silica material employed in my novel process can vary considerably depending on the same factors upon which the amount of heterogeneous palladium catalyst is based.

The selection of the particular set of operating conditions usually will involve a balancing of production rate versus production yield. In general, higher temperatures will give higher space time yields but lower ethylidene diacetate yields based on the acetic anhydride fed. Also, when both the temperature and alumina concentration are high, undesired side reactions occur resulting in decreased yields. Similarly, the use of both high temperature and pressure causes a significant decrease in the yield of ethylidene diacetate. The decreased yield is believed to be due, at least in part, to hydrogenation of the ethylidene diacetate to ethyl acetate and acetic acid.

The process of the invention is further illustrated by the following examples.

EXAMPLES 1–23

Acetic anhydride (100 g.) was hydrogenated in the presence of various heterogeneous palladium catalysts and silica and silica-alumina materials using different temperatures and total autoclave pressures. The acetic anhydride, palladium catalyst and silica or silica-alumina material were loaded into a 300 ml. Hastalloy B autoclave designed to operate in a rocking mode. The autoclave was purged with 100 psig hydrogen gas pressure at room temperature and then the gas was vented. The autoclave internal pressure was increased to 10 psig by adding hydrogen gas at room temperature. The autoclave was sealed and heated and rocked until reaction temperature was reached, at which time additional hydrogen gas was added to increase the autoclave internal pressure to the predetermined value. The time at which the autoclave internal pressure reached the predetermined value was taken at the start of the reaction time. Reactor pressure was maintained at the preset value during the experiment by adding hydrogen gas at the same rate at which it was consumed by the reactants. When the predetermined reaction time was completed the autoclave was cooled by a stream of cold air. After the gas was vented from the autoclave the reaction product was analyzed by gas chromatographic methods.

In Examples 1-3 the reaction was carried out for 30 minutes using 1.0 g. of 5% palladium on carbon (Englehard Lot 29217) and 5.0 g. of a montmorallite clay containing about 30% alumina, the remainder being bulk silica (Girdler K-10).

In Examples 4-10 and 11-17 the reaction was carried out for 60 minutes using 1.0 g. of 5% palladium and 3% palladium, respectively, on a silica-alumina material (Girdler K-10). These supported catalysts were prepared by impregnating Girdler K-10 montmorallite clay powder with the appropriate amount of palladium nitrate solution (10% Pd, Mathey-Bishop Company) diluted with 50 ml. water. The water was evaporated on a steam bath and the catalyst was reduced for 2.5 hours at 300° C. in a flowing hydrogen stream in a tube furnace.

Examples 7-10 and 14-17 are repetitive runs using in each the same catalyst. In those examples, at the end of each run the product mixture was removed from the autoclave by means of a filter leg with a metal frit on the end leaving the catalyst in the autoclave. Fresh acetic anhydride was added to the autoclave and the procedure described above was repeated.

Examples 18-23 were 60-minute runs using 1.0 g. of 5% palladium on carbon and the following materials:
Example 18 100% silica (Davidson 62 Silica Gel).
Example 19 Kieselguhr, about 6% alumina bulk silica (Girdler).
Example 20 Silica-alumina, about 35% alumina, bulk silica (Davison Fine 13 Silica Alumina).
Example 21 Silica alumina, about 25% alumina, bulk silica (Zeolon H, Norton Company).
Example 22 Silica alumina, about 32% alumina, bulk silica (American Cyanamid).
Example 23 Silica alumina, about 36% alumina bulk silica (Davison XZ-36 Silica Alumina).

Table I shows the temperature (°C.) and total pressure (psig) used, the amounts (in moles) of acetic acid (HOAc) and ethylidene diacetate (EDA) produced and the amount of acetic anhydride ($Ac_2O$, in moles) recovered.

TABLE I

| Example | Temperature | Pressure | HOAc | $Ac_2O$ | EDA |
|---|---|---|---|---|---|
| 1 | 120 | 1500 | .49 | .15 | .35 |
| 2 | 150 | 2000 | .80 | — | .31 |
| 3 | 180 | 2000 | .85 | — | .22 |
| 4 | 120 | 1000 | .12 | .76 | .10 |
| 5 | 150 | 1000 | .29 | .34 | .28 |
| 6 | 180 | 1000 | .40 | .25 | .30 |
| 7 | 150 | 1000 | .31 | .45 | .24 |
| 8 | 150 | 1000 | .26 | .55 | .21 |
| 9 | 150 | 1000 | .21 | .67 | .14 |
| 10 | 150 | 1000 | .20 | .70 | .15 |
| 11 | 120 | 1000 | .11 | .82 | .07 |
| 12 | 150 | 1000 | .21 | .55 | .25 |
| 13 | 180 | 1000 | .54 | .07 | .36 |
| 14 | 150 | 1000 | .27 | .40 | .25 |
| 15 | 150 | 1000 | .22 | .52 | .21 |
| 16 | 150 | 1000 | .19 | .60 | .17 |
| 17 | 150 | 1000 | .17 | .66 | .16 |
| 18 | 180 | 2000 | .20 | .83 | .02 |
| 19 | 180 | 2000 | .44 | .54 | .13 |
| 20 | 180 | 2000 | .47 | .37 | .20 |
| 21 | 180 | 2000 | .34 | .24 | .19 |
| 22 | 180 | 2000 | .62 | .24 | .24 |
| 23 | 180 | 2000 | .39 | .57 | .15 |

The invention has been described in detail with particular reference to preferred embodiments thereof, but it will be understood that variations and modifications can be effected within the spirit and scope of the invention.

I claim:

1. Process for the preparation of ethylidene diacetate which comprises hydrogenating acetic anhydride at about 100° to 200° C. and about 250 to 3000 psig in the presence of a catalytic amount of a heterogeneous palladium catalyst and a silica-alumina material which contains about 5 to 40 weight percent alumina and in the substantial absence of strong protonic acid.

2. Process according to claim 1 wherein the catalyst is a supported palladium catalyst.

3. Process according to claim 1 for the preparation of ethylidene diacetate which comprises hydrogenating acetic anhydride at about 100° to 200° C. and about 250 to 3000 psig in the presence of a catalytic amount of a palladium on carbon catalyst and a silica-alumina material containing about 5 to 40 weight percent alumina.

4. Process according to claim 1 for the preparation of ethylidene diacetate which comprises hydrogenating acetic anhydride at about 130° to 160° C. and about 500 to 1200 psig in the presence of a catalytic amount of palladium on carbon catalyst and a silica-alumina material containing about 15 to 30 weight percent alumina.

5. Process according to claim 1 for the preparation of ethylidene diacetate which comprises hydrogenating acetic anhydride at about 100° to 200° C. and about 250 to 3000 psig in the presence of a catalytic amount of a palladium on silica-alumina supported catalyst, the silica-alumina support containing about 5 to 40 weight percent alumina.

6. Process according to claim 1 for the preparation of ethylidene diacetate which comprises hydrogenating acetic anhydride at about 130° to 160° C. and about 500 to 1200 psig in the presence of a catalytic amount of a palladium on silica-alumina supported catalyst, the silica-alumina support containing about 15–30 weight percent alumina.

* * * * *